United States Patent
Suhonen

(12) 
(10) Patent No.: US 6,174,515 B1
(45) Date of Patent: Jan. 16, 2001

(54) TOOTHPASTE COMPOSITION

(75) Inventor: Christopher H. Suhonen, Alto, MI (US)

(73) Assignee: Amway Corporation

(*) Notice: Under 35 U.S.C. 154(b), the term of this patent shall be extended for 0 days.

(21) Appl. No.: 09/587,723

(22) Filed: Jun. 5, 2000

(51) Int. Cl.⁷ ...................................................... A61K 7/16
(52) U.S. Cl. .................................................................. 424/49
(58) Field of Search ........................................... 424/49.58

(56) References Cited

U.S. PATENT DOCUMENTS

| | | | |
|---|---|---|---|
| 3,105,013 | * 9/1963 | Saul et al. | 167/93 |
| 3,282,792 | * 11/1966 | Fiscella | 167/93 |
| 3,934,000 | 1/1976 | Barth . | |
| 4,100,269 | 7/1978 | Pader . | |
| 4,108,979 | * 8/1978 | Muhler et al. | 424/49 |
| 4,118,471 | 10/1978 | Pensak . | |
| 4,122,163 | * 10/1978 | Muhler et al. | 424/52 |
| 4,122,164 | 10/1978 | Mitchell et al. . | |
| 4,144,322 | 3/1979 | Gordon et al. . | |
| 4,156,717 | 5/1979 | Wason . | |
| 4,168,301 | 9/1979 | Pugh et al. . | |
| 4,170,634 | 10/1979 | Cordon . | |
| 4,177,258 | 12/1979 | Gaffar et al. . | |
| 4,187,288 | 2/1980 | Cordon et al. . | |
| 4,212,856 | 7/1980 | Hoyles . | |
| 4,264,579 | 4/1981 | Carr . | |
| 4,303,641 | 12/1981 | DeWolf, II et al. . | |
| 4,414,199 | * 11/1983 | Strubridge | 424/52 |
| 4,428,928 | * 1/1984 | Muhler et al. | 424/52 |
| 4,459,283 | 7/1984 | Harvey et al. . | |
| 4,460,565 | 7/1984 | Weststrate et al. . | |
| 4,485,089 | 11/1984 | Leipold . | |
| 4,490,353 | 12/1984 | Crawford et al. . | |
| 4,529,584 | 7/1985 | Mulvey et al. . | |
| 4,529,585 | 7/1985 | Hayes . | |
| 4,556,553 | 12/1985 | Suganuma et al. . | |
| 4,576,816 | 3/1986 | Suganuma et al. . | |
| 4,581,228 | 4/1986 | Suganuma et al. . | |
| 4,594,242 | 6/1986 | Naganuma et al. . | |
| 4,612,191 | 9/1986 | Yeh et al. . | |
| 4,623,536 | 11/1986 | Winston et al. . | |
| 4,632,826 | 12/1986 | Plöger et al. . | |
| 4,693,888 | 9/1987 | Miyahara et al. . | |
| 4,726,943 | 2/1988 | Klueppel et al. . | |
| 4,871,396 | * 10/1989 | Tsujita et al. | 424/49 |
| 4,877,602 | 10/1989 | Uematsu et al. . | |
| 4,935,226 | 6/1990 | Duckworth . | |
| 4,986,981 | 1/1991 | Glace et al. . | |
| 5,032,383 | 7/1991 | Evans et al. . | |
| 5,039,514 | 8/1991 | Evans et al. . | |
| 5,279,814 | 1/1994 | Wuelknitz et al. . | |
| 5,605,677 | 2/1997 | Schumann et al. . | |
| 5,647,903 | 7/1997 | McGill et al. . | |
| 5,688,492 | 11/1997 | Galley et al. . | |
| 5,718,885 | 2/1998 | Gingold et al. . | |
| 5,728,825 | 3/1998 | Wong . | |

* cited by examiner

*Primary Examiner*—Shep K. Rose
(74) *Attorney, Agent, or Firm*—Brinks Hofer Gilson & Lione; G. Peter Nichols

(57) ABSTRACT

A toothpaste composition comprising a kaolin and a non-abrasive silica. The kaolin is the sole abrasive present in the composition. The composition has an RDA less than about 110.

6 Claims, No Drawings

TOOTHPASTE COMPOSITION

BACKGROUND OF THE INVENTION

This invention relates to a gentle abrasive toothpaste containing calcined kaolin and a hydrating silica gel. More particularly, this invention relates to a toothpaste containing calcined kaolin as the sole abrasive therein, and having low abrasivity while maintaining desirable rheological properties.

The function of abrasives in toothpaste formulations for use in the oral cavity is to remove various deposits, including pellicle film, from the surface of the teeth. Pellicle film is tightly adherent and is partly responsible for the yellow or brownish discoloration of the teeth. A toothpaste therefore should be abrasive enough to maximize removal of this film and other undesired deposits without causing undue abrasion to the surface of the tooth. Dental research is continually concerned with developing toothpaste compositions that demonstrate satisfactory levels of cleaning and that are not unduly abrasive and damaging to the teeth.

U.S. Pat. No. 4,122,163 discloses a toothpaste using calcined kaolin as an abrasive. The kaolin is said to be predominantly of the gamma alumina or mullite form.

U.S. Pat. No. 4,414,199 discloses a toothpaste using calcined kaolin as an abrasive. The kaolin is at least 80% calcined to the mullite crystal form and has a particle size distribution such that more than 50% of the particles are between 1 to 10 microns and less than 5% exceed 10 microns. These toothpastes have a Radioactive Dentin Abrasion of about 124 as determined by the Radioactive Dentin Abrasion Index.

Merely reducing the level of kaolin in the toothpaste formulation results in lower abrasivity, but results in the need for increased levels of conventional thickeners such as gums or other solids such as alumina, calcium carbonate, calcium pyrophosphate, and dicalcium phosphate. An increased level of thickeners in the toothpaste formulation, however, imparts a greater degree of stringiness to the toothpaste and results in poor toothpaste break off properties (the ability of the toothpaste to cleanly come away from the tube when applied to a toothbrush).

Adding other solids such as calcium carbonate, calcium pyrophosphate, and dicalcium phosphate may provide a desirable rheology and break off properties, but they may reduce the availability of soluble fluoride ion because they react with fluoride. Moreover, these solids have inherently high abrasives qualities, which makes their use undesirable. Accordingly, it is a primary object of this invention to produce toothpaste compositions having reduced abrasivity, without sacrificing desirable rheological properties or fluoride availability.

SUMMARY OF THE INVENTION

The present invention relates to a fluoride toothpaste composition having low abrasivity. More specifically, the present invention relates to a toothpaste containing a novel combination of at least one nonabrasive silica and where the kaolin is the sole abrasive present in the toothpaste. Advantageously, the resulting toothpaste has a radioactive dentin abrasive (RDA) index of not more than 110.

The term "sole abrasive" as used in the detailed description and the appended claims means that the composition does not contain more than 5% of another abrasive material.

All percentages used in the detailed description and the appended claims refer to percent by weight unless specifically stated otherwise.

DETAILED DESCRIPTION OF THE INVENTION

The toothpaste composition of the present invention comprises a novel combination of kaolin with a nonabrasive silica gel, wherein the kaolin is the sole abrasive in the composition.

The toothpaste comprises from about 1% to about 50% by weight of kaolin, preferably from about 5% to about 20%, more preferably from about 8% to about 12%. In addition, the kaolin is the sole abrasive present in the toothpaste composition.

The toothpaste also includes at least one non-abrasive silica gel. The non-abrasive silica gel is incorporated into the toothpaste composition in an amount from about 1% to about 50% by weight, preferably from about 5% to about 20%, more preferably from about 10% to about 15%.

Within these ranges, it has been found that the desirable abrasive properties can be achieved when the ratio of the kaolin to the non-abrasive silica is in the range from about 40:1 to about 1:20, preferably from about 10:1 to about 1:3, more preferably from about 2:1 to about 1:2. Most preferably, the ratio of kaolin to hydrated silica is about 1:1.3.

The kaolin used in the toothpaste of the present invention is at least 80%, and most preferably, at least 90%, calcined to the mullite crystal form. Calcination to the mullite form occurs upon gradual heating of uncalcined kaolin to about 975° to about 990° C. Desirably, the kaolin is of a relatively pure grade. In addition, the kaolins useful in the present invention have a whiteness index of at least about 20 or below, and preferably about 13 or below. Suitable kaolins include those manufactured and sold under the trademarks Satintone Special from Englehard Minerals, Al-Silate-o from Freeport, and Optiwhite from Burgess Pigments. Of course, kaolins from other manufacturers may be suitable so long as it is calcined to a level of at least 80%. Kaolin manufacturers are identified in Soap & Cosmetics (December 1999), the relevant contents of which are incorporated herein by reference.

The non-abrasive silica gels used in the toothpaste of the present invention are the amorphous silicas also known as hydrated silica gels. The hydrated silica gels are those having a high silica ($SiO_2$) content material, preferably at least 99% $SiO_2$, and are substantially nonabrasive. The nonabrasive silica gel preferably has a radioactive dentin abrasion index of 25 or less, more preferably 20 or less. The suitable silica gel has an average particle size of about 8.0 to about 12.0 microns. Suitable nonabrasive gels are sold under the trademark Sylodent 15 from W. R. Grace and Huber-Zeodent 165.

The preferred silicas are those that are considered to be the "gel-type" as opposed to the precipitated or fumed type of silicas.

In addition to the above-described essential components, the toothpaste composition of the present invention can contain a variety of optional toothpaste ingredients, some of which are described below.

For example, the toothpaste may include a source of fluoride. A wide variety of fluoride containing materials can be used as a source of fluoride in the toothpaste compositions of the present invention. Examples of suitable fluoride containing materials are found in U.S. Pat. No. 3,535,421 and U.S. Pat. No. 3,678,154, both of which are incorporated herein by reference. Representative fluoride ion sources include: sodium fluoride, stannous fluoride, potassium fluoride, sodium monofluorophosphate amine fluorides and mixtures thereof. Sodium fluoride is particularly preferred.

The desired level of fluoride in the toothpaste composition is such that the composition contains about 0.1% fluoride by weight of the composition. The amount is the maximum allowed by the FDA in an over-the-counter fluoride toothpaste. Accordingly, sodium fluoride may be incorporated into the toothpaste composition in an amount of about 0.245% by weight of the composition. This will provide about 0.11% fluoride ion by weight of the composition.

Humectants may be incorporated in the toothpaste compositions of the present invention. Humectants are used to retain moisture in the toothpaste, particularly at the nozzle end of the tube where the toothpaste can be in prolonged contact with the air. Suitable humectants include glycerin, sorbitol, propylene glycol, other edible polyhydric alcohols, or mixtures thereof, which are admixed with a suitable humectant vehicle, such as water. Humectants are present in the toothpaste composition at a level of from about 15% to about 70%.

Water is also generally present in the toothpaste compositions of the present invention. Water used in the preparation of commercially suitable toothpastes should preferably be deionized and free of organic impurities. Water generally comprises about 5% to about 40% by weight of the toothpaste compositions herein.

Suitable surfactants for used in the toothpaste compositions of the present invention include, but are not limited to, anionic, cationic, nonionic, and amphoteric, surfactants, especially anionic surfactants having detergent and foaming properties.

Preferred anionic surfactants useful herein include the water-soluble salts of alkyl sulfates having from 10 to 18 carbon atoms in the alkyl radical and the water-soluble salts of sulfonated monoglycerides of fatty acid having 10 to 18 carbon atoms. Sodium lauryl sulfate, sodium n-lauroyl sarcosinate, and sodium coconut monoglyceride sulfonates are examples of anionic surfactants of this type. Mixtures of anionic surfactants can also be used.

Preferred cationic surfactants useful in the present invention can be broadly defined as derivatives of aliphatic quaternary ammonium compounds having one long alkyl chain containing from about 8 to 18 carbon atoms, such as lauryl trimethylammonium chloride; cetyl pyridinium chloride; cetyl trimethylammonium bromide; di-isobutylphoxyethyl-dimethylbenzylammonium chloride; coconut alkyltrimethylammonium nitrite; etc. Especially preferred are the quaternary ammonium fluorides described in U.S. Pat. No. 3,535,421 and incorporated herein by reference, where said quaternary ammonium fluorides have detergent properties. The cationic surfactant can also act as germicides in certain of the toothpastes herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants only with this limitation in mind.

The amphoteric surfactants suitable for use in the present invention can be broadly described as derivatives of aliphatic secondary and tertiary amines in which the aliphatic radical can be straight chain or branched and wherein one of the aliphatic substituents contains from about 8 to 18 carbon atoms and one contains and anionic water-solubilizing group, for example, carboxylate, sulfonate, sulfate, phosphate, or phosphonate.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The surfactant can be present in the toothpaste composition of the present invention in an amount from about 0.05% to about 5.0%.

Additional ingredients useful in the toothpaste compositions of the present invention include flavoring agents; sweetening agents; antibacterial agents; coloring agents; binding agents; and preservatives. Any of these materials can be present in the toothpaste of this invention in an amount up to about 5% so long as they do not detract from the novel and advantageous benefits of the present invention.

Suitable binding agents useful in toothpaste compositions of the present invention include alkali metal carboxymethyl celluloses, hydroxyethyl celluloses, hydroxyethyl carboxymethyl celluloses, natural and synthetic gums, polyvinyl pyrrolidone, starch, water soluble hydrophilic colloidal carboxyvinyl polymers, seaweed colloids and mixtures thereof. In a preferred embodiment, the binder comprises a carboxymethyl cellulose material.

Suitable flavoring agents include oils of wintergreen, peppermint, spearmint, sassafras, clove, and cinnamon. Suitable sweetening agents include saccharin, dextrose, levulose, aspartame, D-tryptophan, acetosulpham, dihydrochalcones, and sodium cyclamate.

Preservatives such as methyl paraben, propyl paraben, and sodium benzoate; and antibacterial agents, such as zinc citrate dihydrate, para-chlorophenyl biguanide, 4-chlorobenzylhydryl biguanide, and 5,6-dichloro-2-guanidinobenzimidazole may also be present in the toothpaste compositions of the present invention.

EXAMPLES

The following examples illustrate, but do not limit, the present invention. Unless otherwise indicated, all parts and percentages are by weight.

Example 1

A preferred fluoride toothpaste made in accordance with the present invention is shown below, with acceptable ranges shown.

| FLUORIDE TOOTHPASTE | | |
|---|---|---|
| | % W/W | Range % |
| Sorbitol (70% solution) | 43.024 | 5–70 |
| Deionized water | 20.000 | q.s. |
| Silica gel with an RDA of 20 or less (most preferably Sylodent ® 15) | 13.000 | 5–15 |
| At least 80% calcined kaolin (most preferably Satintone Special ™) | 10.000 | 5–20 |

-continued

FLUORIDE TOOTHPASTE

| | % W/W | Range % |
|---|---|---|
| Glycerin | 5.000 | 3–70 |
| Propylene glycol | 2.500 | 0.05–10 |
| Sodium Lauryl Sulfate | 1.700 | 0.05–5 |
| Polyethylene glycol-8 | 1.000 | 0.05–5 |
| Xylitol | 1.000 | 0.05–5 |
| Flavoring agent | 0.850 | 0.05–5 |
| Sodium carboxymethyl cellulose | 0.800 | 0.05–5 |
| Sodium saccharin | 0.200 | 0.05–5 |
| Sodium phosphate | 0.200 | 0.05–5 |
| Sodium fluoride | 0.245 | 0.05–1 |
| Zinc citrate dihydrate | 0.180 | 0.01–5 |
| Methyl paraben | 0.150 | 0.01–5 |
| Propyl paraben | 0.050 | 0.005–5 |
| Xanthan gum | 0.100 | 0.01–5 |
| Coloring agent | 0.001 | 0.00001–2 |

The glycerin, sorbitol, and propylene glycol act as humectants. The glycerin and sorbitol also serve as sweeteners. The carboxymethyl cellulose is a binder. Sodium lauryl sulfate is a surfactant. Sodium saccharin is the primary sweetener. Zinc citrate dihydrate is an astringent and antimicrobial. Sodium phosphate is added as a pH buffer. Methyl paraben and propyl paraben are both preservatives. Any of a variety of flavoring or coloring agents can be used.

Once prepared, the toothpaste composition has a pH from about 4 to about 8. Fluoride toothpastes providing pH values within the 4.0 to 8.0 range provide especially effective dental enamel antisolubility benefits compared to toothpastes with pH values outside this range.

The Radioactive Dentin Abrasion (RDA) of the toothpaste of the present invention is 110 or less, preferably 90 or less, and most preferably 80 or less. Preferably, the RDA is between about 50 and about 80.

Example 2

Radioactive Dentin Abrasion tests were performed on a toothpaste composition of the present invention and compared to the RDA of two commercially available toothpaste products.

In the United States, tooth dentine abrasion is typically measured by the ADA recommended procedure to determine the RDA index. The abrasion measured is related to the abrasiveness of a standardized comparative paste, and is expressed as a percentage value. Extracted human teeth are irradiated to convert the phosphorus 31 naturally present in the hydroxylapatite of the tooth to radioactive phosphorus 32. The specimens (teeth) are mounted in methylmethacrylate so that they would fit in a V-8 cross-brushing machine. The specimens were brushed using a slurry consisting of 10 g ADA reference material in 50 ml of a 0.5% CMC glycerin solution for 1500 strokes as preconditioning. The brushes used were those specified by the ADA and the brush tension was 150 g.

Following the preconditioning, a sandwich test design was used where a toothpaste according to Example 1 (Formula B of Example 3) 25 g per 40 ml water) was flanked by the reference material slurry (10 g per 50 ml of 0.5% CMC solution).

After brushing for 1500 strokes (using the ADA specified brush with 150 g tension), one milliliter sample was taken, weighed, and added to 5 mls. of scintillation solution. The sample was thoroughly mixed and put on a scintillation counter to detect the radiation. The net counts per minute (CPM) for the sample were divided by the weight of the sample to calculate a net CPM per gram of slurry. The net CPM/g of the pre and post ADA reference material for each test slurry was calculated and then averaged to use to calculation the RDA of the sample. The ADA material was assigned a value of 100 and its ratio to the sample was calculated.

The RDA value for the use of a toothbrush with water alone is about 15. The RDA of the toothpaste composition of the present invention was 73.3±1.7, as compared to 104.1±2.2 for Crest® Regular.

Example 3

Radioactive Dentin Abrasion tests were performed on toothpaste compositions of the present invention where the kaolin and non-abrasive silica were varied as shown in the following table.

| Ingredient | A (wt. %) | B (wt. %) | C (wt. %) |
|---|---|---|---|
| Water | 20 | 20 | 20 |
| Sorbitol | 29.0245 | 43.0245 | 46.0245 |
| Na saccharin | 0.2 | 0.2 | 0.2 |
| NaF | 0.245 | 0.245 | 0.245 |
| Na phosphate. | 0.2 | 0.2 | 0.2 |
| FD&C BLUE #1 | 0.0005 | 0.0005 | 0.0005 |
| Xylitol | 1 | 1 | 1 |
| Zinc citrate | 0.18 | 0.18 | 0.18 |
| Propylene glycol | 2.5 | 2.5 | 2.5 |
| m paraben | 0.15 | 0.15 | 0.15 |
| p paraben | 0.05 | 0.05 | 0.05 |
| Glycerin | 5 | 5 | 5 |
| PEG 8 | 1 | 1 | 1 |
| Xanthan | 0.1 | 0.1 | 0.1 |
| Na CMC | 0.8 | 0.8 | 0.8 |
| Non-abrasive hydrated silica gel (Sylodent 15) | 0 | 13 | 20 |
| Kaolin (Engelhard LS928) | 37 | 10 | 0 |
| Sodium lauryl sulfate | 1.7 | 1.7 | 1.7 |
| flavor | 0.85 | 0.85 | 0.85 |
| Total | 100 | 100 | 100 |

The results are set forth in the following table.

| | Formula A | Formula B | Formula C |
|---|---|---|---|
| Hydrated silica | 0 | 13 | 20 |
| Kaolin | 37 | 10 | 0 |
| RDA | 124 | 74 | 20 |

Thus, it can be seen that according to the present invention by selecting the ratio of the hydrated silica and the kaolin an advantageous abrasive property can be achieved.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

I claim:

1. A toothpaste composition having reduced dentin abrasivity comprising from about 1% to about 50% by weight of calcined kaolin as the sole abrasive, wherein the calcined kaolin is at least 80% calcined to the mullilte crystal form, and from about 1% to about 50% by weight of a nonabrasive hydrated silica gel, wherein the toothpaste composition has a radioactive dentin abrasion index of not more than 110.

2. The toothpaste composition of claim 1 wherein the nonabrasive hydrated silica gel has a radioactive dentin abrasion index of less than 20.

3. The toothpaste composition of claim 1 wherein the calcined kaolin is present in an amount from about 5% to about 20% by weight.

4. The toothpaste composition of claim 3 where the nonabrasive hydrated silica gel is present in an amount from about 5% to about 20% by weight.

5. The toothpaste composition of claim 1 wherein the ratio of kaolin to non-abrasive silica is from about 40:1 to about 1:20.

6. The toothpaste composition of claim 1 further comprising fluoride.

\* \* \* \* \*